United States Patent [19]

Guild

[11] 3,956,940

[45] May 18, 1976

[54] SAMPLING OF FLUID

[76] Inventor: Lloyd V. Guild, 358 Church Road, Bethel Park, Pa. 15102

[22] Filed: May 5, 1975

[21] Appl. No.: 574,269

[52] U.S. Cl. .............................. 73/421.5 R; 73/28
[51] Int. Cl.² .......................................... G01N 1/22
[58] Field of Search ............ 73/28, 421.5; 137/525; 417/567; 23/254 R

[56] References Cited
UNITED STATES PATENTS

| | | | |
|---|---|---|---|
| 1,321,062 | 11/1919 | Lamb et al. | 23/254 R |
| 1,621,498 | 3/1927 | Drager | 137/525 |
| 2,707,074 | 4/1955 | Tussey | 137/525 |
| 2,809,589 | 10/1957 | Randolph | 137/525 |
| 3,093,001 | 6/1963 | Williams | 73/421.5 R |
| 3,410,059 | 11/1968 | Garnier | 73/421.5 R |
| 3,802,250 | 4/1974 | Garnier | 73/421.5 R |

*Primary Examiner*—S. Clement Swisher
*Attorney, Agent, or Firm*—Hymen Diamond

[57] ABSTRACT

A sampler including a pump unit and a holder for an adsorbent for the pollutants both carried by the personnel while in the area under observation, typically during an 8-hour working period. The pump unit includes a motor-driven pump which draws the air breathed by the personnel through the adsorbent while the personnel is in the area. The unit includes a counter for counting the revolutions of the motor as a measure of the air being drawn. At the end of the working period, the adsorbent is desorbed and the quantity of pollutants determined. This apparatus is of very low power so that it can be carried without discomfort for a working day, and low quantities of air are pumped. High efficiency and low leakage is achieved with a unique pump. The pump includes a plenum whose pressure is varied by flexing a thin membrane. The flow of air to and from the plenum is controlled by unique valves, an outlet valve connected to the plenum and an intake valve to the adsorbents. Each valve includes a plate having an opening in airflow communication with the plenum with a protuberance around the hole on one face of the plate. A thin strip of resilient material is stretched over the hole engaging the protuberance. When the pressure in the plenum is increased by flexing the membrane, so as to reduce the volume of the plenum, the valve connected to the plenum is opened, exhausting the air producing the excess pressure and the valve connected to the adsorbents closed. When the membrane is flexed in the opposite direction, the pressure in the plenum is reduced, the valve connected to the plenum is closed, and the valve connected to the adsorbent is opened, and contaminated air is drawn through the adsorbent.

16 Claims, 17 Drawing Figures

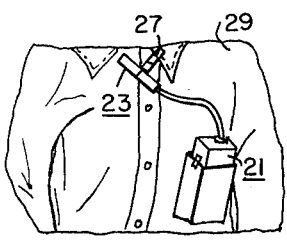
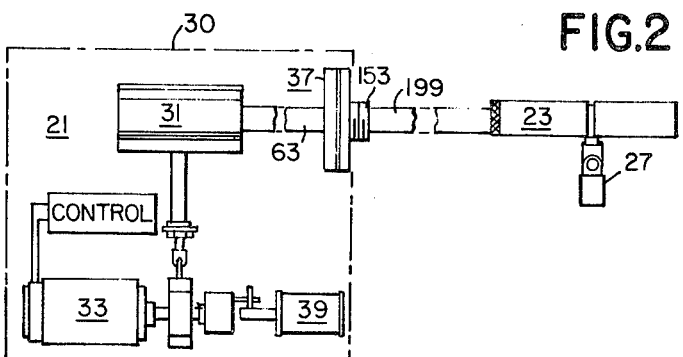
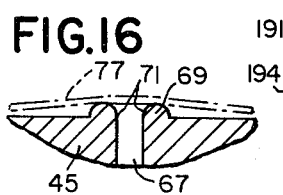
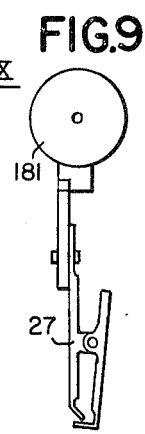
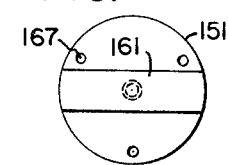
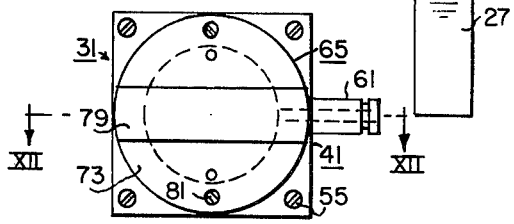
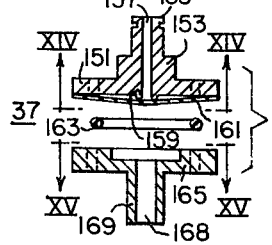
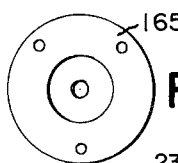
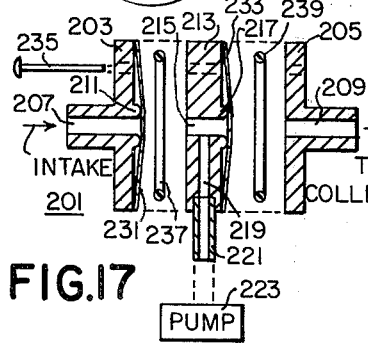
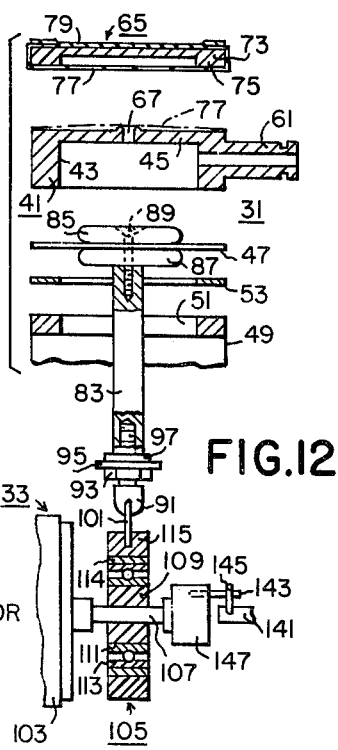
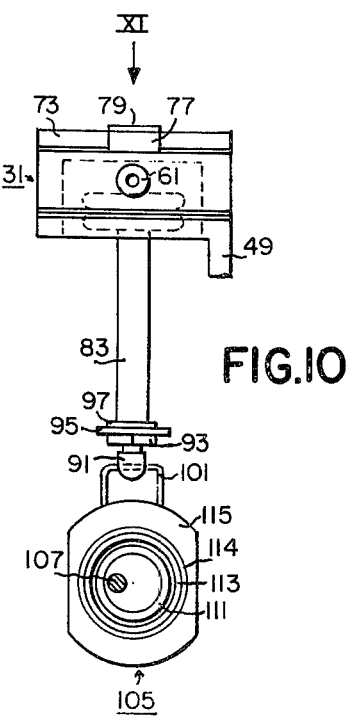

SAMPLING OF FLUID

BACKGROUND OF THE INVENTION

This invention relates to the art of sampling fluids for selected components, such as contaminants or pollutants, and has particular relationship to such sampling in whose practice the content of the components in the fluid is to be precisely determined. In the interest of facilitating the understanding of this invention, the invention is herein described as applied to concrete situations: the protection of industrial workers against chemicals such as vinyl chloride and the others listed in Guild U.S. Pat. No. 3,870,492, particularly as required by the Occupational Safety and Health Act (OSHA — Act 91-596) and the carrying out of air pollution studies. In following this practice, it is not intended in any way to restrict the scope of this invention.

In the area of Industrial Hygiene described above and in certain air pollution studies, it is necessary to repeatedly collect air samples of relatively low volume over long time periods. Typically, in an industrial plant, a worker may, during the time that he is in the plant, which may be 6 or 8 hours or longer, repeatedly collect samples of 1 milliliter to 200 milliliters per minute of the air which he breathes. The collection must be effected with apparatus, operating accurately, and typically including a pump unit and an adsorbent. The worker must be capable of carrying this apparatus continuously while in the plant. This apparatus must be automatically operable without attention from the worker while he attends to his assigned duties and indeed without the worker having to be conscious as to its operation.

It is accordingly an object of this invention to meet the above conditions and to provide apparatus of light weight capable of being carried, with the same absence of attention as he wears an article of clothing, by personnel in a region under observation during long periods of time, and which apparatus shall be capable of operating efficiently and accurately without attention of the personnel carrying the apparatus to collect selected pollutants from samples of repeated low-volume flow of the air in the region.

It is another object of this invention to provide such apparatus including a pump and valves which shall be driven from a low-power rechargeable battery with a minimal drain on the battery and in whose operation the air leakage from the pump and valves shall be minimized.

SUMMARY OF THE INVENTION

In accordance with this invention, air sampling apparatus is provided including a pump having a plenum whose pressure is varied by a thin diaphragm or membrane driven through a rod by an eccentric from a high-efficiency motor. The diaphragm is composed of thin latex, typically neoprene, stiffened by a cork ring secured to it. The portion of the membrane suspended from the cork ring is baggy. The material should be capable of withstanding many flexations (typically 1,000,000) without fatigue. The flow of air (or other fluid) in and out of the plenum is controlled by valves. Each valve includes a plate having an opening serving as a passage for the air in or out of the plenum. A thin strip of resilient material, typically latex, such as is used for making prophylactics, is stretched across the plate closing the opening. The strip is tensioned. In the case of one valve, the strip is across the surface of the plate remote from the plenum. In this case, when the pressure within the plenum exceeds the pressure outside of the plenum, the strip is retracted from the opening and air flows out of the plenum, and when the pressure in the plenum is less than the pressure outside of the plenum, the strip is sucked into the opening, sealing the opening so as to prevent air from flowing out of the plenum. In the other valve, the strip is across the surface of the plate nearest the opening, and when the plenum pressure exceeds the pressure outside the valve, this valve is sealed, and when the pressure outside exceeds the pressure in the plenum, it is opened. Since the air flow is of very low volume and low leakage is desired, it is necessary to effectively seal the opening in each valve when air flow is to be prevented. It has been discovered that with a protuberance completely around the opening, serving as a seat for the valve, an unusually effective seal is achieved. An effective seal would also be provided in other ways, for example, by giving the surface of the plate, which is engaged by the strip, a conical shape coverging towards the opening or by providing a highly smooth and clean surface.

Since the strips of the valves, which constitute their movable actuating parts, are thin and the membrane is also thin, the energy which these components absorb from the battery in being driven is very low. Drain of the battery is minimized. Further improvement is achieved by connecting the rod, which drives the membrane, to the eccentric through a swivel joint permitting the eccentric end of the rod to pivot in a plane generally perpendicular to the plane of the membrane about an axis generally perpendicular to the drive shaft. The quantity of air pumped by the pump is measured by a motor-revolution counter. The drive shaft of the motor is connected to the counter through pins which are physically separate. The pin from the motor shaft engages the pin connected to the counter shaft and pushes it around.

BRIEF DESCRIPTION OF THE DRAWINGS

For a better understanding of this invention, both as to its organization and as to its method of operation, together with additional objects and advantages thereof, reference is made to the following description, taken in connection with the accompanying drawings, in which:

FIG. 1 is a view in perspective showing the principal components of this invention and the manner in which it is used;

FIG. 2 is a generally diagrammatic view showing the apparatus according to this invention;

FIG. 7 is a view, partly in side elevation and partly in longitudinal section, of the adsorbing unit of the apparatus shown in FIGS. 1 and 2;

FIG. 8 is a view in end elevation taken in the direction of the arrow VIII of FIG. 7;

FIG. 9 is a view in end elevation taken in the direction of the arrow IX of FIG. 7;

FIG. 10 is a view in side elevation showing the pump of the pump unit and its eccentric drive;

FIG. 11 is a plan view taken in the direction of the arrow XI of FIG. 10;

FIG. 12 is an exploded view in section taken along line XII—XII of FIG. 11 showing the pump of the pump unit and also showing the connection of the pump to its drive;

FIG. 13 is an exploded view in longitudinal section of the additional valve of the pump unit;

FIG. 14 is a plan view taken in the direction of arrows XIV—XIV of FIG. 13;

FIG. 15 is a plan view taken in the direction of the arrows XV—XV of FIG. 13;

FIG. 16 is a fragmental enlarged view showing a feature of the valves according to this invention; and FIG. 17 is an exploded view in longitudinal section showing predominantly a push-pull valve in accordance with this invention.

DETAILED DESCRIPTION OF INVENTION

Figure 3:
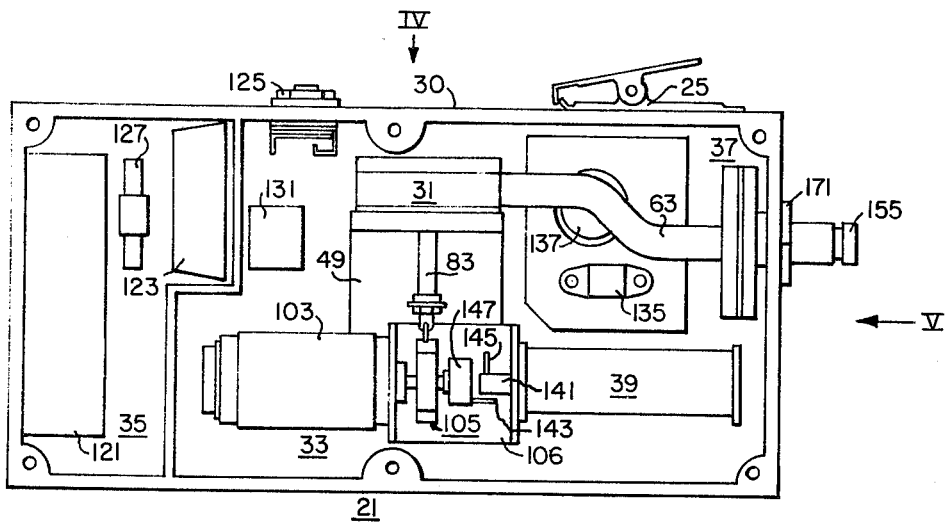
FIG. 3 is a plan view of the pump unit with the cover removed of the apparatus shown in FIGS. 1 and 2.
Figure 4:
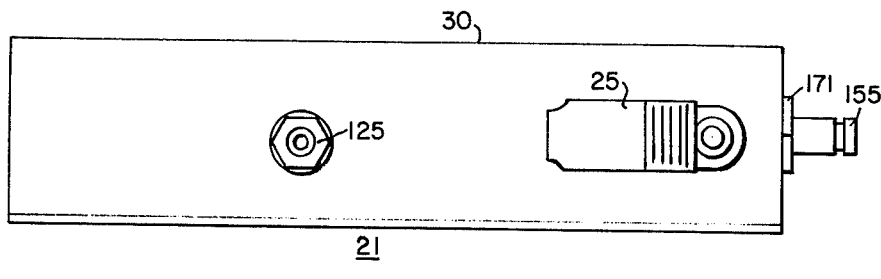
FIG. 4 is a view in side elevation of the unit shown in FIG. 3 taken in the direction of the arrow IV.
Figure 5:
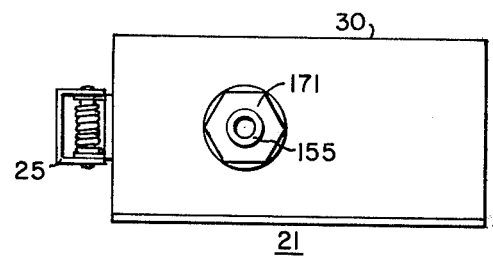
FIG. 5 is a view in end elevation of the unit shown in FIG. 3 taken in the direction of the arrow V.
Figure 6:
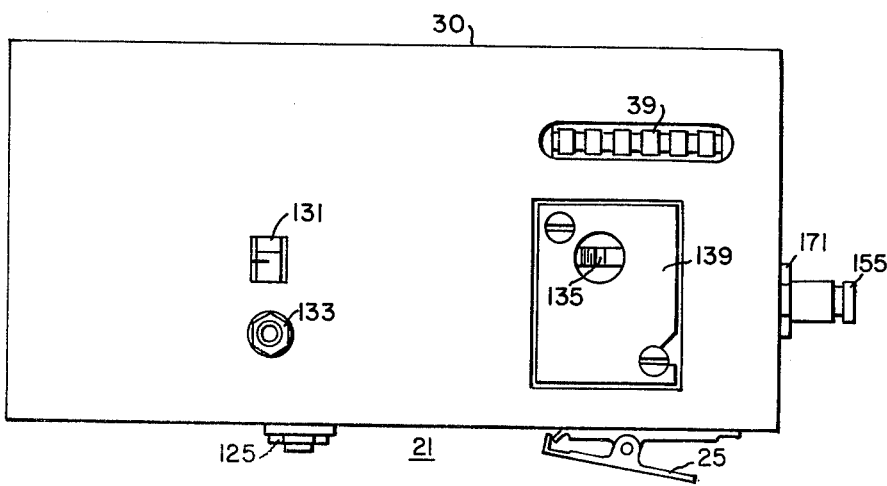
FIG. 6 is a plan view of the face of the unit shown in FIG. 3 opposite the open face.

FIGS. 1 through 16 show sampling apparatus including a pump unit 21 and an adsorbent unit 23. The units 21 and 23 are each provided with a clip 25 (FIG. 3) and 27. The pump unit 21 is inserted in and clipped to the pocket of the personnel 29 using the apparatus and the adsorbent unit is clipped to his collar. Typically, the complete apparatus weighs about 10 ounces. The personnel 29 in a short time becomes accustomed to carrying the apparatus and is oblivious of its pressure.

The pump unit (FIG. 3) includes a container 30, within which there are a pump 31, a drive 33 for the pump, a power supply 35, an intake valve 37, an indicator 39, and auxiliary components not shown in detail. The container 30 is composed of light-weight material, such as aluminum or plastic.

The pump 31 (FIG. 12) includes a plenum 41 of generally square cross-section bounded by side walls 43, a plate 45 and a membrane or diaphragm 47. The plate 45 may be integral with the walls 43. The membrane 47 is composed of a resilient material, such as neoprene. Typically, the thickness of the membrane 47 is about 0.005 inch.

The pump 31 is supported on an L-shaped bracket 49. The foot of the bracket 49 has a circular opening 51. The membrane 47 is provided with a supporting or stiffening ring gasket or washer 53, typically of cork for ease of handling and alignment. The membrane 47 and gasket 53 are compressed between the portion of the foot of bracket 49 bounding opening 51 and the end of the wall 43. The membrane 47 is provided on its upper surface with a sealing adhesive so that it is sealed to the end of wall 43. The membrane 47, the plate 45, the walls 43, the washer 53 and the foot of bracket 49 are held together by corner bolts (FIG. 4) 55.

From the wall 43, an inlet tube 61, terminating in a fitting, extends. This tube 61 is connected to the intake valve 37 (FIG. 3) by a flexible cable 63.

The pump 31 includes an outlet valve 65 (FIGS. 11, 12) for which the plate 45 bounding the plenum provides a seat. The plate 45 has an opening 67 which, about its outer rim, is provided with a protuberance 69 (FIG. 16). The protuberance 69 is generally in the form of a ring of arcuate cross-section with the arc being convexed in the direction away from the plenum. The protuberance 69 joins the inner wall of the opening 67 in an arcuate surface 71 of very small radius, typically about 0.005 inch.

The valve 65 also includes a plate or disk 73 of circular section having a circular cavity. Across the rin 75 bounding the cavity in the disk 73 a thin strip 77 of a resilient material, such as latex, is stretched. The strip 77 is tensioned. It is passed over the top of the disk 73 and its ends are secured by a strip 79 of adhesive. The disk 73 is secured to the plate 45 by bolts 81, and when the disk is so secured, the strip 77 covers the opening 67 and is stretched and bowed across the protuberance 69 (FIG. 16). This last position of the strip 77 is shown in broken lines in FIG. 12. The protuberance 67 serves as a seat for the opening and closing mechanism of the valve 65.

The opening 67 must be of small area typically a circular hole of 1/16 inch or less is suitable. The strip 77 has a thickness of less than 0.004 inch, and is 3/16 inch to ¼ inch wide, having about the same width relative to the width of plate 45 as the strip 79. The protuberance 69 has a height above plate 45 of about 0.006 inch to 0.012 inch.

The strip 77 normally closes valve 65. The pressure on the strip 77 required to open the valve 65 is determined by two factors: the extent to which the strip 77 is tensioned or stretched and the heighth of the protuberance 69. When the pressure in the plenum 41 is reduced, the portion of the strip which engages the protuberance is sucked into the opening 67. The arcuate junction 71 between the protuberance 69 and the inner wall of the opening 67 prevents the thin strip 77 from being ruptured by the junction of the opening 67 and the protuberance 69.

The membrane 47 is flexed inwardly and outwardly of the plenum 41 by a rod 83. The membrane 47 is secured between disks 85 and 87 which together with the membrane are secured to the end of the rod 83 by a bolt 89 (FIG. 12). At its other end, the rod 83 is internally threaded. A bolt 91 having a dome-shaped head is secured into the end of the rod 83, and is securely held by a nut 93 which compresses a washer 95 against a shoulder 97 on the end of rod 83. The bolt 91 may be screwed into the end of the rod 83 an appropriate distance to achieve the desired throw of the membrane 47. Thus the throw of the rod 83 is adjustable. The head of the bolt 91 has an opening through which passes the cross-bar of a U-shaped or hairpin connector 101 (FIGS. 10, 12) between the drive 35 and the rod 83. The bar of the connector is of smaller diameter than the opening in the head so that the bolt 91 and the arm are capable of pivoting about the cross-bar in a plane perpendicular to the membrane 47.

The drive 33 includes a highly efficient motor 103 and an eccentric 105. The motor is supported on one leg of a U-shaped bracket 106 (FIG. 3) which is mounted on the leg of L-shaped bracket 49. The eccentric 105 is driven from the shaft 107 of the motor 103 through a bushing 109 on which the rotatable race 111 of a ball-bearing is pressed. The non-rotatable race 113 of the ball-bearing is pressed into a bushing 114 in a plate 115 to which the legs of the U-shaped connector are secured. As the shaft 107 is rotated, the plate 115 moves towards and away from the plenum 41 carrying the rod 83 with it and flexing the membrane 47 inwardly and outwardly. The mounting of the head of bolt 91 on the U-shaped connector 101 permits the rod to pivot about an axis perpendicular to the shaft 115.

The power supply 35 includes a low-power battery 121 (FIG. 3) and a regulator 123. Conductors (not shown) from the battery 121 and regulator 123 are interconnected, by a connector 127, with conductors (not shown) from the motor 103 and conductors (not shown) from a socket 125 (FIG. 4) through which the battery is charged. A battery indicator 131, which may be viewed through a window in the front of container 30, is also provided. There is also a test probe 133 (FIG. 6) and a switch 135, and a rheostat 137 for controlling the speed of motor 103 whose adjusting mechanism is covered by plate 139.

The indicator 39 is a counter for counting the revolutions of the motor 103. The counter is driven by a shaft 141 from the motor 103. The drive is through pins 143 and 145 which are physically disconnected but are engaged when the motor is rotated. Pin 143 is carried by a roller 147 which is secured coaxially on the shaft of motor 103. This pin is generally parallel to the shaft 107 of the motor. Pin 145 is carried by shaft 141 generally at right angles to pin 143. When the motor rotates roller 147, pin 143 engages pin 145 causing shaft 141 to rotate and actuate the counter 39.

The intake valve 37 (FIGS. 13, 14 and 15) includes a plate 151 integral with a threaded shoulder 153 from which a fitting 155 extends. An opening 157 extends through the plate 151 and shoulder 153 and fitting 155. About the inner end of the opening 157 there is a protuberance 159, similar to the protuberance 69, in plate 45 (FIG. 16). A thin (less than 0.004 inch) strip 161 of resilient material (latex) is stretched tensioned across plate 151 covering the opening 157 and the protuberance 159. The strip 161 is stretched and tensioned by engagement with an O-ring 163 which is compressed between the plate 151 and a cooperative plate 165 of generally T-section. Plates 151 and 165 are secured together by bolts 167. Plate 165 has a cavity connected through an opening 168 in stem 169 to tube 63 (FIG. 3). A sealed region is defined between the O-ring and plates 151 and 165. The valve 37 is secured to container 30 by a nut 171 which is screwed on shoulder 153 and engages the wall of container 30.

The adsorbing unit 23 (FIGS. 7, 8, 9) is typically composed of plastic and includes a tube 181. The tube 181 has a circumferential notch from which the clip 27 is suspended. The tube 181 has an opening 183 of greater diameter at one end which terminates in an opening 185 of smaller diameter. Near the outer end the wall of the opening 183 is threaded. A member 187 having a thread 189 in the center and a fitting, 191 and 193, to receive a rubber tube at each end is screwed into the tube 181 and is secured by a knurled nut 194. A rubber tube 195 is secured to the fixture 193 at the inner end and a sample collector 197, as disclosed in Guild U.S. Pat. No. 3,870,492, but with the tips 13 and 15 broken off, is secured in the tube 195. The collector 197 extends into the opening 185 fitting snugly, but not tightly, therein. The fitting 191 is connected to the fitting 155 of input valve 37 by a tube 199 (FIG. 2).

OPERATION SAMPLING APPARATUS

Once the sampling apparatus according to this invention is affixed to the personnel 29, the motor 103 is energized and continues to run during his working hours. The motor 103 drives rod 83 which flexes membrane 47 inwardly and outwardly of the plenum 41. When the membrane 47 is flexed inwardly, the pressure in the plenum 41 is increased above the pressure outside retracting the strip 77 from the opening 67 so that air is exhausted from the plenum. At the same time, strip 161 seals the intake opening 157. When membrane 47 moved outwardly, the pressure in the plenum 41 is less than the pressure outside, and strip 77 seals opening 67 while strip 161 is retracted from opening 157. Air flows into the plenum 41 through the charcoal in sampler tube 197 and valve 37. During the next inward movement of the membrane 47, this air is exhausted. This operation continues so long as the personnel 29 is in the area under observation. At the end of this time, the charcoal is removed from tube 197 and analyzed as disclosed in Guild patent.

FIG. 17 shows a push-pull valve 201 including plates 203 and 205 of longitudinal T-section. The stem and center of each plate is penetrated by an axial opening 207 and 209. The plate 203 has a protuberance 211 about opening 207 similar to the protuberance 69 on plate 45 (FIG. 16). Between the plates 203 and 205, there is an intermediate plate 213. The plate 213 has an axial opening 215 terminating in a protuberance 217 on the face remote from plate 203. A lateral opening 219 communicates with the opening 215, and at the opposite end, it communicates with a tube 221 which is connected to a pump 23, typically similar to pump 31.

A thin strip 231 of a resilient material is stretched across the inner surface of plate 203 covering the opening 207. Likewise a thin strip 233 of resilient material is stretched across the surface of plate 213 remote from plate 203 covering the opening 215. The plates 203, 213, 205 are secured together by bolts 235 with O-rings 237 and 239 interposed between plates 203 and 213 and between 213 and 205. The O-rings 237 and 239 tension the strips 231 and 233 respectively. Regions are enclosed between each O-ring 237 and 239 and the adjacent surfaces of plates 203 and 213 and 213 and 205. The opening 207 is connected to the intake which may be the air in a room; the opening 209 is connected to a collector which may be a gas-tight nylon bag carried by the personnel.

OPERATION OF VALVE 201

On the exhaust stroke of the pump 223, strip 233 seals opening 215 and strip 231 is retracted from opening 207. Air flows into the region bounded by O-ring 237. On the compression stroke of the pump, strip 231 seals opening 207 and strip 233 is retracted from opening 215. Air flows through opening 209 into the collector. This flow of the air is repeated so long as the personnel is in the area. At the end of this time period, the bag is removed and the air in it analyzed by a chromatograph or the like.

While preferred embodiments of this invention have been disclosed, many modifications thereof are feasible. This invention is not to be restricted except insofar as is necessitated by the spirit of the prior art.

I claim:
1. Apparatus, capable of being readily carried by personnel, for sampling a fluid for at least one selected component in said fluid over a relatively long period of time, the said apparatus including a pump having:
   a. a plenum to contain said fluid,
   b. a membrane connected to said plenum actuable to flex to increase and decrease the pressure of said fluid in said plenum, and
   c. a valve, said valve including:
      1. a first plate having an opening of small area therein through which fluid to or from said plenum may be transmitted, and
      2. a first tensioned strip of yieldable resilient material stretched over and adjacent to the surface of said plate and over said opening, whereby when the difference between the fluid pressure in said plenum and the fluid pressure on the surface of said strip opposite said opening is of one polarity, the portion of said strip over said opening is sucked into said opening and seals said opening preventing the flow of fluid to or from said plenum through said opening, and when said difference is of the opposite polarity, said strip is retracted from said opening permitting the flow of fluid to or from said plenum through said opening; said first strip being positioned over said opening so that it is retracted from said opening when the pressure in said plenum is increased and seals said opening when the pressure in said plenum is decreased, Said apparatus also including means, connected to said membrane, for actuating said membrane to alternately increase and decrease the fluid pressure in said plenum respectively above and below the pressure on said opposite surface of said strip, during successive intervals during said time period, and means, connected to said plenum, for supplying said fluid to said plenum during the intervals during which the pressure in said plenum is decreased, the said supplying means including:

a. additional valve means for preventing flow of fluid through said supplying means during the intervals during which said pressure in said plenum is increased and for permitting the flow of fluid to said plenum during the intervals during which the pressure in said plenum is decreased, said additional valve means including:

1. a second plate having an opening of small area therein through which fluid to or from said plenum may be transmitted, and 2. a second tensioned strip of yieldable resilient material stretched over and adjacent to the surface of said plate and over said last-named opening, whereby when the difference between the fluid pressure in said plenum and the fluid pressure on the surface of said second strip opposite said last-named opening is of said one polarity, the portion of said second strip over said last-named opening is sucked into said last-named opening and seals said last-named opening preventing the flow of fluid to or from said plenum through said last-named opening, and when said difference is of said opposite polarity, said second strip is retracted from said last-named opening permitting the flow of fluid from said plenum through said last-named opening, said second strip being positioned over said last-named opening so that it seals said last-named opening when the pressure in said plenum is increased and and is retracted from said last-named opening when the pressure in said plenum is decreased, and b. means for collecting said component from said fluid during the intervals during which said fluid is supplied.

2. The apparatus of claim 1 wherein the first and second plates each includes a protuberance about the opening extending from the surface over which the associated strip is stretched to tension the portion of the associated strip over the opening and to effectuate the sealing of the openings by the associated strips when the difference between the pressure in the plenum and the pressure on the surface of each strip opposite the plenum is of the one polarity.

3. The apparatus of claim 1 wherein the actuating means for the membrane includes a rod connected to said membrane, a motor, and a driving connection between the motor and the rod, said driving connection including a linkage near the end of said rod nearest the motor permitting pivotal movement of said end with reference to an axis generally at right angles to the drive shaft of said motor.

4. The apparatus of claim 3 wherein the driving connection between the motor and the rod includes an eccentric and the linkage is pivotally connected between the eccentric and the end of the rod permitting the rod to pivot in the plane generally perpendicular to the membrane about its connection to the linkage as an axis.

5. The apparatus of claim 1 including an indicator driven by the motor for indicating the quantity of fluid passing through the plenum, the drive shaft of the motor having a driving pin extending therefrom generally parallel to the shaft and the driven shaft of the indicator having a driven pin extending transversely to the drive shaft, said driving pin and driven pin being physically disconnected from each other, but said driving pin being engageable with said driven pin to drive said indicator.

6. Apparatus for sampling a fluid including a plenum, a first plate having an opening of small area connected to said plenum for transmitting fluid to and from said plenum, said opening being bounded by a protuberance, a first strip of thin yieldable resilient material stretched over and adjacent to the surface of said plate and over said opening and said protuberance tensioning the portion of said strip over said opening; said strip being positioned on the side of said plate remotest from said plenum, so that when the fluid pressure in said plenum exceeds the pressure on the side of said strip remotest from said plenum, said strip is retracted from said opening and said fluid is transmitted through said opening, and when the fluid pressure in said plenum is less than the fluid pressure on said side of said strip remotest from said plenum, the portion of said strip over said protuberance and opening is sucked into said opening and seals said opening and the transmission of fluid through said opening is prevented, a second plate connected to said plenum having an opening for transmitting fluid to and from said plenum, said last-named opening being bounded by a protuberance and a second strip of thin, yieldable, resilient material covering said opening in said second plate "said last-named protuberance tensioning the portion of said strip over said last-named opening; said second strip being positioned on the side of said second plate nearest said plenum," so that when the fluid pressure in said plenum exceeds the pressure on the side of said second strip remotest from said plenum, the portion of said second strip over said last-named protuberance and opening is sucked into said last-named opening and seals said last-named opening preventing transmission of fluid to said plenum, and when the fluid pressure in said plenum is less than the pressure on said side of said second strip remotest from said plenum, said second strip is retracted from said opening and said last-named opening is opened transmitting fluid to said plenum.

7. A low-leakage valve for fluid including a plate having an opening of small area therein and a tensioned strip of thin, yieldable, resilient material stretched over and adjacent to the surface of said plate and over said opening so that when the pressure of said fluid on one surface of said plate exceeds the pressure of said fluid on the opposite surface of said plate, the portion of said strip over said opening is sucked into said opening and seals said opening, preventing the flow of fluid therethrough, and when the pressure of said fluid on said opposite surface of said plate exceeds the pressure on said one surface of said plate, said strip is retracted from said opening, permitting the flow of fluid through said opening.

8. The valve of claim 7 wherein the plate has a protuberance about the opening on the surface where the opening is covered by the strip, said protuberance extending from said surface and being engaged by said strip and the portion of said strip over said opening being tensioned by said protuberance to effectuate the sealing of said opening.

9. A valve including a first plate having a first opening of small area therein, a first tensioned strip of thin, yieldable resilient material stretched over a surface of said first plate and covering said first opening on said surface, a second plate disposed adjacent to said first plate on the side of the surface of said first plate covered by said first strip, said second plate having a second opening of small area therein, a second tensioned strip of thin, yieldable resilient material stretched over the surface of said second plate remotest from said first strip, said second strip covering said second opening, and means sealing the space between said plates to form a region between said plates, whereby when the fluid pressure in said region exceeds the fluid pressure outside of said region, said second strip is retracted from said second opening permitting fluid to flow through said second opening out of said region, and said first strip is sucked into said opening and seals said first opening preventing fluid from flowing through said first opening into said region, and when the fluid pressure in said region is less than the fluid pressure outside of said region, said first strip is retracted from said first opening permitting fluid to flow through said first opening into said region, and said second strip is sucked into said opening and seals said second opening preventing fluid from flowig from said region through said second opening.

10. The apparatus of claim 1 including a low-power battery for supplying energy to said apparatus, and wherein the membrane and the strip are thin to minimize the absorption of energy from said battery.

11. The apparatus of claim 1 including a low-power battery for supplying energy to drive the membrane and wherein the membrane, the strip of the valve of the pump and the strip of the additional valve are thin to minimize the drain of energy from the battery.

12. The apparatus of claim 10 wherein the battery has a voltage of about 1.4 volts and supplies current of about 50 milliamperes to the apparatus and the membrane and strip have a thickness of about 0.005 inch.

13. The apparatus of claim 11 wherein the battery has a voltage of about 1.4 volts and supplies current of about 50 milliamperes to drive the membrane and the membrane and strips each has a thickness of about 0.005 inch.

14. The apparatus of claim 1 including means for setting the amplitude of the flexing of the membrane at a predetermined magnitude.

15. The apparatus of claim 1 wherein the flexing of the membrane is carried out by a rod connected to the membrane, the said apparatus also including an eccentric drive for the rod, said rod being connected to said drive through a bolt in the end of the rod nearest the eccentric, the position of said bolt in the end of the rod being adjustable.

16. Apparatus, capable of being carried by personnel, for sampling fluid for at least one selected component in said fluid over a relatively long period of time, the said apparatus including means to be contacted by said fluid for collecting said componenet from said fluid, a pump connected to said collecting means for pumping said fluid through said collecting means, a motor for driving said pump, an indicator to determine, from the operation of said motor, the quantity of fluid transmitted through said collecting means, and the motor has a drive shaft for driving an indicator and the indicator has a driven shaft, a first pin extending from said drive shaft, a second pin extending from said driven shaft, said pins being at an angle less than 180° to each other and said first pin being connectable in driving relationship with said second pin while remaining physically disengageable therefrom.

* * * * *